United States Patent [19]

Fleer

[11] 4,182,038
[45] Jan. 8, 1980

[54] DENTAL HANDPIECE

[75] Inventor: Ernst O. Fleer, Bensheim-Auerbach, Fed. Rep. of Germany

[73] Assignee: Siemens Aktiengesellschaft, Berlin & Munich, Fed. Rep. of Germany

[21] Appl. No.: 752,905

[22] Filed: Dec. 21, 1976

[30] Foreign Application Priority Data

Dec. 22, 1975 [DE] Fed. Rep. of Germany ....... 2558064

[51] Int. Cl.² ............................................... A61C 1/10
[52] U.S. Cl. ...................................... 433/85; 433/126
[58] Field of Search .................... 285/134, 136; 32/27, 32/26

[56] References Cited

U.S. PATENT DOCUMENTS

| | | | |
|---|---|---|---|
| 3,032,878 | 5/1962 | White | 32/27 |
| 3,125,809 | 3/1964 | White | 32/27 |
| 3,349,490 | 10/1967 | Lieb et al. | 32/28 |
| 3,858,323 | 1/1975 | Flatland | 32/27 |
| 3,894,338 | 7/1975 | Loge | 32/27 |
| 3,909,047 | 9/1975 | Salmela | 285/282 |
| 4,007,529 | 2/1977 | Fleer | 32/27 |
| 4,075,761 | 2/1978 | Behne | 32/27 |

Primary Examiner—Robert Peshock
Attorney, Agent, or Firm—Hill, Van Santen, Steadman, Chiara & Simpson

[57] ABSTRACT

A dental handpiece which has a connecting fitting for attachment to a supply hose having at least one agent supply line, a head section having a compressed air drive motor, a grip portion extending between the fitting and head section and a passage in each of said head section, grip portion and fitting for compressed air and a separate passage in each of these for any additional desired agents, characterized by the grip portion having a tubular sleeve portion, which is connected to the head section and receives the passage for compressed air and any other passages for agents, if present, and means detachably connecting the grip portion to the connecting fitting and includes means enabling relative rotation of the sleeve portion to the fitting so that the sleeve portion and each passage of the head section are rotatable relative to the fitting and each passage therein. Preferably, the head section and the sleeve portion are a single component and the handpiece will include a valve means for controling the flow of at least one of the agents to the head section.

7 Claims, 4 Drawing Figures

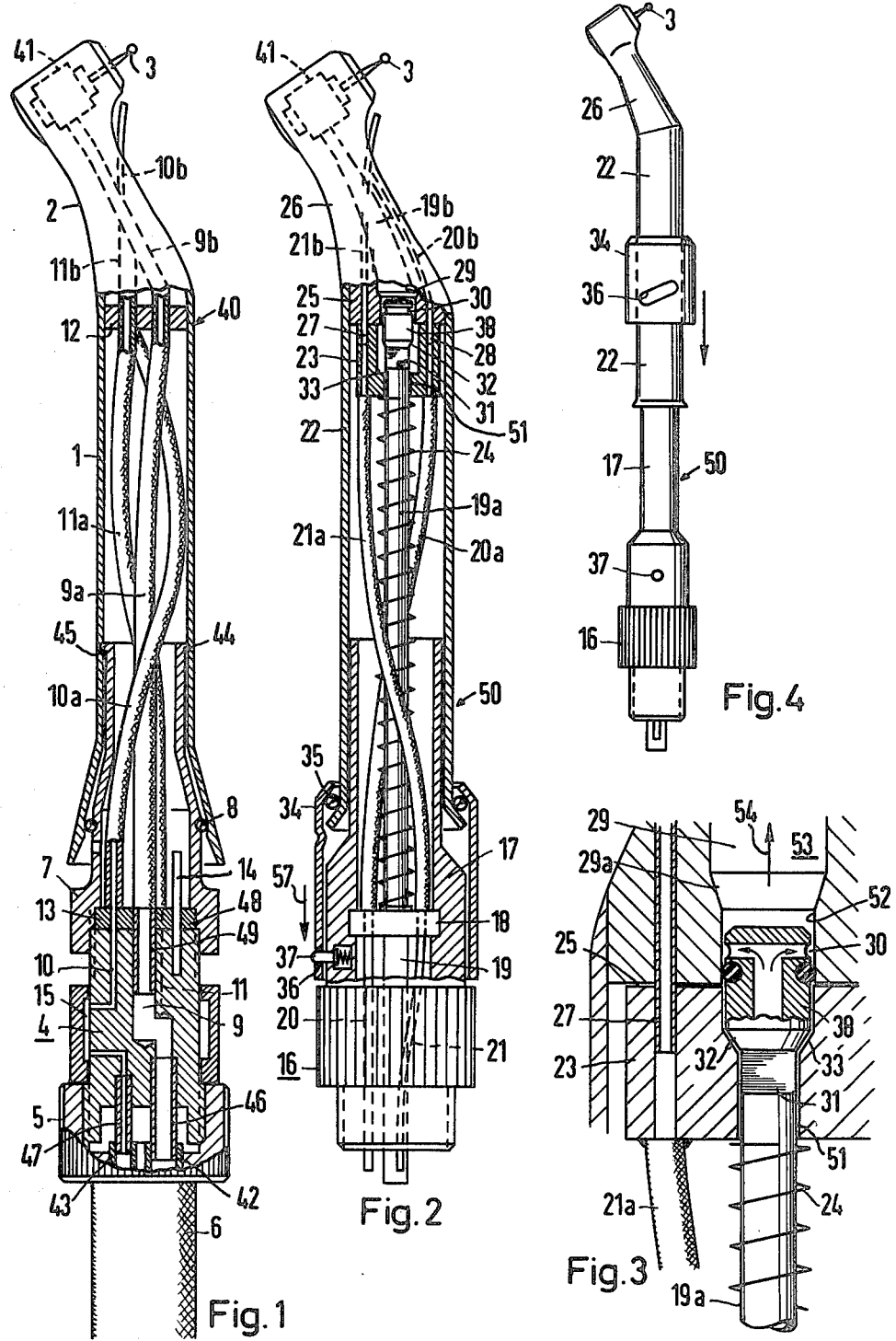

DENTAL HANDPIECE

BACKGROUND OF THE INVENTION

The present invention is directed to a dental handpiece having a head section, which contains a motor or turbine driven by compressed air, a grip portion extending from the head section to a connecting fitting, which is adapted for connection to a hose which has a compressed air supply line and a separate supply line for each additional agent that is desired. The compressed air and other agents, if present, are conveyed to the head section by interconnected passages which are arranged in the head section, grip portion and connecting fitting of the handpiece.

The present invention proceeds from the fact that the supply hose of a dental handpiece of a known construction produces an interferring torsional moment during manual manipulation of the handpiece of an operator who must compensate for this torsional moment by applying a greater counter-moment with his fingers. In order to avoid this disadvantage, it is known to provide so-called rotary coupling, which is a separate component, between the supply hose and the handpiece. The addition of this coupling or joint provides a further separating point or point in addition to those separation points already present in the known handpiece structures, for example, the joint between the grip portion and the head section. With the addition of this additional component, the cost of producing the handpiece or the handpiece arrangement, respectively, is increased. The presence of this additional component will increase the length of the handpiece and create an additional disadvantage, which is that this lengthening of the handpiece will strongly impair the manipulability of the handpiece.

In addition to the above-mentioned rotational coupling or joint, it is also desirable to provide the dental handpiece with a throttle valve or choker valve in order to enable changing or controlling the pressure of one of the agents. For example, the controlling of the pressure of the compressed air will enable the changing of the number of revolutions of the air driven motor. In order to provide the throttle or choker valve, a known solution provides an intermediate piece or component between the supply hose and the handpiece. The intermediate piece has a rotatable concentric ring and a valve which will vary the flow cross section of a passage in response to rotation of the concentric ring. By the addition of this separate component containing the throttle or choker valve, the handpiece arrangement is further lengthened and is thus extremely unwieldy. As a consequence of the significantly longer lever arm of the handpiece on which the weight of the supply hose is applied, a much greater pitching moment will act on the handpiece and must be compensated by a correspondingly greater counter-force from the operator's fingers grasping the handpiece.

SUMMARY OF THE INVENTION

The present invention is directed to providing a dental handpiece which does not exhibit the above-mentioned disadvantages and which is more economical to manufacture. The dental handpiece of the present invention has a structure which reduces the length of the handpiece to reduce the interferring torsional and pitching moment which acts on the handpiece. The dental handpiece of the present invention provides a structure which also reduces the necessity of providing too many separation and connecting points or joints which joints will increase the cost of manufacturing the handpiece. In addition, the present invention provides the structure which has space economy and enables providing means for changing the rate of flow and thus the rotational speed of the drive by a valve means in the handpiece without increasing the overall length of the entire handpiece.

To accomplish these objects, the dental handpiece of the present invention provides an improvement in a handpiece which has a connecting fitting for attachment to a supply hose having at least one agent supply line, a head section having a compressed air drive motor or turbine, a grip portion extending between the fitting and head section, and means for conveying at least one agent including compressed air from the supply hose into the head section, said means comprising a passage for each agent in the fitting, grip portion and head section. The improvement in this handpiece comprises the grip portion having a tubular sleeve portion being connected to the head section and receiving some passages therein and means detachably connecting said grip portion to the connecting fitting and including means enabling relative rotation of the sleeve portion to the fitting so that the sleeve portion and each passage of the head portion are rotatable relative to the fitting and each passage therein.

It should be known that the means for detachably connecting is intended to denote means which the customer or operator, in contrast to a maintenance expert, can easily operate on the spot without requiring special tools to disconnect the grip portion from the fitting. Thus, the grip portion with the attached head section can be easily removed from the fitting when desired.

It is significant in terms of the present invention that the rotary joint is arranged between the tubular sleeve portion of the grip portion and the connecting fitting or base of the handpiece and that the rotary joint simultaneously serves the purpose of enabling the separation of the section containing the drive motor or turbine from the connecting fitting. It is thereby possible to use one connecting fitting with different handpiece grip portions with their attached head sections which have different drives with regard to either their type of mounting or their performance data. The removability of the handpiece grip portion from the fitting directly in the area of the rotary joint permits the construction of grip portions and head sections as a one-piece component which has the advantage that the previous conventional separating point in the form of screw connections on the head section can be eliminated. Thus, a smoother surface is thereby produced in this portion or area of the handpiece than was present in the previously known handpieces. A further significant advantage of the structure of the present invention is that the section of the handpiece which comes into contact with either the physician or the patient can be removed entirely from the connecting fitting and sterilized.

The present invention enables production of a series of different handpiece embodiments having a minimum number of components and also separation joints. All of these embodiments have the same overall length regardless of whether they have a volume flow control valve for the compressed air, a cooling agent, or are provided with any one of the several different types of drive motors such as ball bearing turbines or air bearing turbines. The invention also enables the production of grip portions and connecting fittings or sections which are also interchangeable.

BRIEF DESCRIPTION OF THE DRAWINGS

FIG. 1 is a longitudinal cross-sectional view with portions in elevation for purposes of illustration of an embodiment of a dental handpiece in accordance with the present invention;

FIG. 2 is a longitudinal cross-sectional view with portions in elevation for purposes of illustration of a different embodiment of a handpiece constructed in accordance with the present invention;

FIG. 3 is an enlarged partial cross section of a flow control valve of the embodiment of FIG. 2; and FIG. 4 is an illustration of the embodiment of FIG. 2 in a partially disassembled state.

DESCRIPTION OF THE PREFERRED EMBODIMENTS

The principles of the present invention are particularly useful when incorporated in a dental handpiece generally indicated at 40 in FIG. 1. As illustrated, the handpiece 40 has a detachable grip portion or sleeve which has a sleeve portion 1, which has one end connected to a head section 2. The head section 2 contains a compressed air drive turbine or motor 41, which drives or rotates an instrument such as a drill or burr 3.

The grip portion extends from the head section 2 and is detachably connected to a connecting fitting 4 which is the base section of the handpiece. The fitting 4 is detachably connected by a packing nut 5 to a supply hose 6, which has supply lines such as a compressed air supply line 42 and a water supply line 43.

The grip portion is detachably connected to the fitting 4 by means including a sleeve member 7, which is threadably received on the fitting 4, and the member 7 has a tubular portion telescopically received in the sleeve portion 1 of the grip sleeve to enable relative rotation of the sleeve portion 1 about its longitudinal axis of the handpiece relative to the connecting fitting 4 without any axial movement. For this purpose, ball bearings 8 are provided between the sleeve member 7 and the sleeve portion 1 of the grip portion. In addition, the sleeve member 7 at one end has a small annular bulge or rib 44 which is engaged in the matched ring groove 45 provided on the interior surface of the sleeve portion 1 and thus prevents a sliding off of the sleeve portion 1 from the sleeve member 7.

The handpiece 40 has means for conveying compressed air and at least one additional agent if desired. As illustrated, this means comprises a passage 9 in the fitting 4, which has a hollow tube or prong 46 in communication with compressed air supply line 42, passage 10, which has a hollow tube or prong 47 in communication with the water supply line 43 and a passage 11 for cooling air which is in communication with a cooling air supply line (not illustrated) in the supply hose 6. In a similar manner, the sleeve portion 1 receives three flexible hoses 9a, 10a and 11a which are in communication, respectively, with the passages 9, 10 and 11 and also in communication with passages 9b, 10b and 11b in the head section 2. Thus, compressed air for driving the turbine 41 is received from the supply line 43 and conveyed by the passages 9, 9a, 9b to the turbine. The passages 10b and 11b in the head section 2 are joined together and terminate in a common small tube which is directed at the instrument 3 so that air and water are mixed in this small tube to form a cooling spray.

The hoses 9a, 10a and 11a at one end extend through and are supported by a disk-shaped mounting support 12 which is rigidly inserted in the sleeve portion 1. The hoses 9a, 10a and 11a are connected with the passages 9b, 10b and 11b either at the support 12 or after passing through the support 12. On the opposite end, an additional or support disk 13 receives or supports the end of the flexible hoses 9a, 10a and 11a. The disk or centering piece 13 as illustrated is held on an end face 48 of the fitting 4 and is centered thereon by a rigid connecting piece or tubular prong 49 of hose 9a and a pin 14 extending through the disk 13 and into the fitting 4 so that the passages of the hoses 9a, 10a and 11a are in alignment with the passages 9, 10 and 11 in the fitting 4.

As mentioned, the individual passages or line sections 9a through 11a are flexible hoses which are freely laid without any support in the tubular sleeve member 7 and the tubular sleeve portion 1. Each of the hoses has a length that exceeds the axial distance between the support section 12 and the disk 13 to enable relative rotation between the disk 13 and the section 12.

By providing the hose 9a with the projecting rigid connecting piece or prong 49, the prong 49 is inserted into the passage 9 of the fitting 4. Thus, when assemblying or attaching the grip portion onto the fitting 4, the prong 49 is received in the passage 9 and the pin 14 is received in its socket to provide the desired alignment between the passages 9, 10 and 11 of the fitting 4 and the hose sections 9a through 11a.

The fitting 4 receives a ring 15 which overlies two ports in the passage 10. The ring 15, which rotates on the fitting 4, has an internal groove that covers the ports and has a changing cross section. By rotating the ring 15 on the fitting, the flow of the agent, such as water, in the passage 10 can be changed and controlled and thus the coaction of the ring 15 and ports of passage 10 forms a throttle or choke valve.

The hose section 9a for the compressed air is illustrated as being centrally or axially disposed on the disk 13 with the other hoses 10a and 11a being wrapped therearound. If desired, the hose 9a may be replaced by a rigid tube; however, this will require the end extending to the support section 12 to be centrally positioned and provided with suitable sealing means.

During forming of the connection between the grip portion and the fitting 4, the disk 13 which is attached to the ends of the passages 9a through 11a is oriented by means of the centering pin 14 and is placed on the surface 48 of the connecting fitting 4. The sleeve member 7, when threaded on the fitting 4, will press the disk 13 against the surface 48 of the fitting 4 and in this manner produces a connection with corresponding line sections 9 through 11. When the grip portion is rotated, hoses 9a through 11a will twist without any contraction of their cross section occurring. In this way, the group of flexible hoses 9a, 10a and 11a permits a rotatability of the sleeve portion 1 relative to the sleeve member 7 and the connecting fitting 4 of approximately 360°.

As illustrated, the grip portion and the head section 2 are preferably formed as a one-piece construction. Thus, precisely those portions of the external surfaces of the grip portion and head section, which portions come into contact with a patient or are touched by the hands of the dentist can be separated all in one piece from the connecting fitting 4 and, if necessary, be either disinfected or sterilized. The use of the rotary coupling joint as a separation between the grip portion on the one hand and the connecting fitting on the other hand makes it possible to eliminate the previously required additional separation point between the head section 2 and the grip portion. In this manner, a much smoother transition can be produced between the head section 2 and the sleeve portion 1 of the grip portion. For example, screw threads and other undercuttings for the purpose of threading the head section onto a grip portion may be eliminated.

An embodiment of the handpiece is generally indicated at 50 in FIG. 2. In this embodiment, the handpiece 50 includes a connecting fitting 16, a grip portion having a sleeve portion 22 and a head section 26. As illustrated, the head section 26 is integral with one end of the sleeve portion 22.

To detachably connect the sleeve portion 22 on the fitting 16, the fitting has a tubular sleeve-shaped receiving portion 17 which is telescopically received in the sleeve portion 22. The receiving portion 17 mounts a support piece 18 in which one end of the compressed air passage 19 of the fitting 16 along with the other agent passages 20 and 21 are mounted. The passages 19, 20 and 21 are in communication with passages 19a through 21a. As illustrated, the passages 20a and 21a are flexible hoses which are connected to a disk-shaped centering piece 23 which is engaged on a counter-member 25 that is positioned at a head section 26 end of the sleeve 22. Passage 19a consists of a fixed rigid tube which extends from the support 18 and extends through a guide channel or bore 51 in the centering piece 23. To bias or urge the centering piece 23 against the counter-member 25, a compression spring 24 surrounds the tube 19a. The counter-member 25 has prongs 27 and 28 which are in communication with the passages 21b and 20b, respectively, and when the centering piece 23 engages the counter-piece 25, the prongs 27 and 28 establish a connection with the lines 21a and 20a via corresponding channels in the disk 23.

The rigid tube 19a is arranged in the center of the grip portion and terminates with an end portion or member 38 which is received in a channel 29 which is connected with the passage 19b of the head portion 26. As best illustrated in FIG. 3, the front end of the end portion 38 is closed, but has a cross bore 30 which enables compressed air in the tube 19a to flow into the channel 29 and then into the passage 19b. The elements 29, 30 and 38 form a valve which will vary the flow of compressed air to the drive motor in the head section 26. The actuation of the valve occurs in response to longitudinal displacement or movement of the portion 38 in the passage 29 which movement is due to longitudinal displacement of the sleeve portion 22 on the receiving portion 17 and will be explained in greater detail hereinafter.

As best illustrated in FIG. 3, the rigid tube 19a and the centering piece 23 have means coacting to prevent relative rotation as the centering piece 23 assumes a given axial position on the tube 19a. As illustrated, this means comprises a square cross-sectional portion 31 on the tube 19a which section 31 is received in a corresponding square socket or portion of the channel 51 of the center piece 23. In addition the tube 19a adjacent the square portion 31 has a collar 32 that will engage a corresponding shoulder 33 as the square portion 31 is received in the square bore of the center section 23. It should be noted that the channel 51 may have the square cross section for its entire length or just at that portion adjacent shoulder 33.

As mentioned hereinabove, the sleeve portion 1 of the grip portion is telescopically received on a tubular sleeve portion 17. To hold the sleeve portion 22 on the portion 17, an annular sleeve or connecting piece 34 engages the sleeve portion 22 by means of ball bearings 35 so that it is free to rotate thereto. The sleeve 34 is provided with an elongated hole or slot 36 (FIG. 4) which extends obliquely on the circumference and receives a spring loaded guide pin or detent 37 which is provided in the portion 17.

To remove the sleeve portion 22, the detent 37 is depressed to be disengaged from the slot 36 and the sleeve 34 and the sleeve portion 22 can be quickly removed from the fitting 16. With the removal of the sleeve portion 22 from the connecting fitting 16, pressure spring 24 presses guide section 23 with the attached flexible hoses or lines 20a and 21a away from the support piece 18 until the collar 32 of the tube 19a engages or rests against the corresponding constructed shoulder 33. In this position, the means for preventing relative rotation comprising the square portion 31 is engaged in a square portion of the guide channel 51 of the section 23, so that the rotation of the section 23 relative to the tube 19a is prevented. When the sleeve portion 22 of the grip tube is received on the portion 17 of the fitting 16, the disk 23 with the lines 20a and 21a cannot be rotated relative to the connecting fitting 16 until the disk has assumed the position such as illustrated in FIG. 2. Marking points may be arranged on the sleeve portion 22 as well as on the connecting fitting 16 and these marking points will enable further simplification of the insertion of the sleeve portion 22 on the portion 17 as well as the formation of the coupling of the passages 19a, 20a and 21a to passages 19b, 20b and 21b of the head section 26. When the sleeve portion 22 is telescopically placed over the portion 17 of the connecting fitting 16, tube end 38 will be received in the passage or bore 29 and the connecting pieces or prongs 27 and 28 will be received in the corresponding channels in the disk 23. If the frontal end surface of the disk 23 rests against the counter-piece 25, further pushing of the sleeve portion 22 on the connecting portions 17 will cause the collar 32 to be lifted from the shoulder 33 and finally the square portion 31 to be disengaged from the square cross section guide portion of the guide channel 51. After the square portion 31 has been disengaged from the guide channel 51 of the guide disk 23, the sleeve portion 22 with the guide disk 23 may be rotated relative to the connecting fitting 16.

In order to reduce frictional losses brought about by the axial contact pressure of the spring 24 on disk 23, a ball bearing or similar friction-reducing element may be arranged between the disk 23 and the spring 24. A similar or suitable friction reducing element may also be arranged between the interior surface of sleeve portion 22 and the exterior surface of sleeve-shaped section 17 of the connecting fitting 16.

The penetration of the end portion 38 of the tube 19a into the channel or bore 29, subsequent to the assembly of the sleeve portion 22 on the connecting fitting 16, is utilized for the purpose of controlling the flow cross section for the compressed air passage. For this purpose, the channel 29 has a small diameter portion 52 connected by a conical section 29a (FIG. 3) to a large diameter portion 53. The diameter of the conical section 29a increases in the direction of arrow 54 which is the direction of the movement toward the drive motor of the head section 26. Thus, the axial position of bore 30 in section 29a will determine the flow cross section of the compressed air. By means of the proper selection of the external diameter of the tube end or portion 38 and small diameter cylindrical section or portion 52 of the channel 29, a minimum amount or quantity of air flowing through the valve can be obtained when the bore 30 is axially positioned in the small diameter portion 52. Depending on the penetration depth of the tube end portion 38 into the section 29a, the size of the flow cross section will be increased and thus the flow rate of the compressed air will be correspondingly changed to create a corresponding change in the rotational speed of the drive motor.

The adjustment of the valve, which is formed by the portion 52, 29a and 53 of the bore 29 and the bores 30 of the end portion 38, occurs by means of varying the axial position of the sleeve portion 22 on the connecting fitting 16. This adjustment of the axial position of portion 22 on portion 17 is achieved by rotation of the sleeve 34. Due to the spring pressure acting on the sleeve portion 22 via piece 23 and 25, the sleeve portion 22 will move in a longitudinal direction of the handpiece as the shell or sleeve 34 is rotated on the portion 17 to move the detent 37 in the slot 36. Rotation of the shell 34 in one direction will cause the shell or sleeve 34 to be moved on the portion 17 in the direction of arrow 57 and thus increase the penetration of the end portion 38 into the passage 29 to increase the flow cross section.

As illustrated in FIG. 4, the shell or sleeve 34 has been completely removed from the portion 17 and shifted along the sleeve portion 27. It should be realized that the connection sleeve 34 can be completely removed from the sleeve portion 22, if desired, by passing it over the head section 26.

Instead of using twistable, flexible line hoses for the passages to transport the various agents in the region of the grip portion, rigidly arranged passages can be utilized. However, the rigid passages will require a connection which will enable rotation between the fitting and grip portion. These connections can be formed by each rigid passage at the coupling location having a port in a member which is in communication with a corresponding concentric ring channel in the other member of the rotary joint. With more than one passage, the ports and concentric ring channels must be in different axial positions or in a step arrangement. A rotary joint using concentric ring channels to form the connection of the passage is more expensive to produce than each of the solutions illustrated in the sample embodiments of the present invention.

Although various minor modifications may be suggested by those versed in the art, it should be understood that I wish to employ within the scope of the patent warranted hereon, all such modifications as reasonably and properly come within the scope of my contribution to the art.

I claim:

1. In a dental handpiece having a connecting fitting for attaching to a supply hose having at least one agent supply line, a head section having a compressed air drive motor, a grip portion extending between the fitting and the head section, and means for conveying at least one agent including compressed air from the supply hose into the head section, said means comprising a passage for each agent in the fitting, grip portion and head section, the improvements comprising said grip portion having a tubular sleeve portion, being integral with the head section and receiving at least one passage therein, and means for detachably connecting said grip portion to the connecting fitting and including a first tubular member and a second tubular member, said first tubular member being connected to the fitting and telescopically receiving the sleeve portion with means providing relative rotation of the sleeve portion to the fitting so that the sleeve portion and each passage of the head section are rotatable relative to the fitting and each passage therein, said second tubular member being telescopically received on said sleeve portion and including bearing means to enable relative rotation on said sleeve portion, said means for detachably connecting including means provided between the first and second tubular members for adjusting the axial position of the sleeve portion to the fitting in response to relative rotation of said second tubular member on said fitting, and one of the passages of the handpiece includes valve means for controlling the flow of the agent in the passage in response to the changes in the axial position of the sleeve portion on the fitting, and means for detachably connecting enabling removal of the integral grip portion and head section from the fitting without requiring any tools.

2. In a dental handpiece according to claim 1, wherein said valve means regulates the amount of compressed air reaching the head section, said valve means including a member attached to said fitting being disposed in a frusto-conical portion of said one passage, so that relative changes in the axial position of the sleeve portion to the fitting causes movement of the member in the frusto-conical portion to control flow of the air.

3. In a dental handpiece according to claim 1, wherein the means for adjusting includes a component part of the second tubular member.

4. In a dental handpiece according to claim 1, wherein the means for conveying conveys compressed air and at least one additional agent, wherein the passage for compressed air received in the sleeve portion is a rigid tube mounted on the connecting fitting and centrally received in the sleeve portion, and the passage for each of said other agents comprises a flexible hose freely arranged along the rigid tube, one end of each of said flexible hoses being rigidly connected to the connecting fitting, the other end of each hose being mounted on a centering piece, said centering piece being guided for relative rotation on the rigid tube and movable therealong to engage a counterpiece of the head section, said rigid tube having an axial portion coacting with the centering piece to prevent relative rotation of the centering piece as the centering piece engages the axial portion.

5. In a dental handpiece according to claim 4, wherein said valve means regulates the amount of compressed air reaching the head section, said valve means including a member attached to an end of said rigid tube and being disposed in a frusto-conical portion of said one passage in said head section, so that relative changes in the axial position of the sleeve portion to the fitting causes movement of the member in the frusto-conical portion to control flow of the air.

6. In a dental handpiece according to claim 4, which includes means biasing the centering piece toward the axial portion of the rigid tube, said axial portion being positioned on the rigid tube so that the centering piece will engage the axial portion as the grip portion is removed from the connecting fitting and will become disengaged from the axial portion when the grip portion is mounted on the fitting.

7. In a dental handpiece having a connecting fitting for attachment to a supply hose having at least two agent supply lines, a head section having a compressed air drive motor, a grip portion extending between the fitting and the head section, and means for conveying at least two separate agents including compressed air from the supply hose into the head section, said means comprising a separate passage for each agent in the fitting, grip portion and head section, the improvements comprising said grip portion having a tubular sleeve portion being integral with the head section and receiving a passage for each agent therein; means for detachably connecting said grip portion to the connecting fitting and including a tubular member being connected to the fitting and being telescopically received in the sleeve portion with means providing relative rotation of the sleeve portion to the fitting so that the sleeve portion and each passage of the head section are rotatable relative to the fitting and each passage therein, said means for detachably connecting enabling removal of the integral grip portion and head section from the fitting without requiring any tools; each passage received in the sleeve portion being a flexible hose which is essentially freely arranged therein, each of the flexible hoses having one end rigidly attached to an end of the sleeve portion adjacent the head section and the other end attached to a passage in a centering piece, said centering piece having means coacting with the fitting to enable alignment of each passage of the centering piece with the respective passage in the fitting, said centering piece being held in engagement with a matching surface of the fitting as the grip portion is connected to the fitting by the detachable connecting means; and said connecting fitting including valve means for controlling flow of an agent in one of said passages, said valve including a sleeve rotatably mounted on said fitting so that relative rotation of the sleeve on the fitting changes the flow rate in said passage.

* * * * *